United States Patent [19]
Springer et al.

[11] Patent Number: 5,948,758
[45] Date of Patent: Sep. 7, 1999

[54] METHODS FOR TREATING VARIOUS DISEASE STATES BY REDUCING ADHESION OF LEUKOCYTES OF TARGET CELLS

[75] Inventors: Timothy Springer, Chestnut Hill; Takashi K. Kishimoto; Thomas M. Roberts, both of Cambridge, all of Mass.

[73] Assignee: Dana Faber Cancer Institute Inc., Boston, Mass.

[21] Appl. No.: 08/811,027

[22] Filed: Mar. 4, 1997

Related U.S. Application Data

[62] Division of application No. 08/223,820, Apr. 6, 1994, Pat. No. 5,739,032, which is a continuation of application No. 07/771,849, Oct. 7, 1991, abandoned, which is a continuation of application No. 07/019,440, Feb. 26, 1987, abandoned.

[51] Int. Cl.$^6$ ..................................................... A61K 38/17
[52] U.S. Cl. ................................................. 514/12; 514/2
[58] Field of Search ............................................ 514/12, 2

[56] References Cited

FOREIGN PATENT DOCUMENTS

| | | |
|---|---|---|
| A-0 362 526 | 4/1990 | European Pat. Off. . |
| A-0 362 531 | 4/1990 | European Pat. Off. . |
| A-0 364 690 | 4/1990 | European Pat. Off. . |
| WO 90/13316 | 11/1990 | WIPO . |

OTHER PUBLICATIONS

Anderson, D. C. et al., "The Severe and Moderate Phenotypes of Heritable Mac–1, LFA–1 Deficiency: Their Quantitative Definition and Relation to Leukocyte Dysfunction and Clinical Features", *J. Infect. Dis.* 152:668–689 (1985).

Barbosa, J. A. et al., "Gene mapping and somatic cell hybrid analyses of the role of human lymphocyte function–associated antigen–3 (LFA–3) in CTL–target cell interactions", *J. Immunol.* 136:3085–3091 (Apr. 1986).

Botstein, D. et al., "Construction of a Genetic Linkage Map in Man Using Restriction Fragment Length Polymorphisms", *Am. J. Hum. Genet.* 32:314–331 (1980).

Gromkowski, S. H. et al., "Functional distinctions between the LFA–1, LFA–2, and LFA–3 membrane proteins on human CTL are revealed with trypsin–pretreated target cells", *J. Immunol.* 134:244–249 (1985).

Hildreth, J. E. K. et al., "The human lymphocyte function–associated (HLFA) antigen and a related macrophage differentiation antigen (HMac–1): functional effects of subunit–specific monoclonal antibodies", *J. Immunol.* 134:3272–3280 (1985).

Hildreth, J. E. K. et al., "A human lymphocyte–associated antigen involved in cell–mediated lympholysis", *Eur. J. Immunol.* 13:202–207 (1983).

Kishimoto, T. K. et al., "Cloning of the β Subunit of the Leukocyte Adhesion Proteins: Homology to an Extracellular Matrix Receptor Defines a Novel Supergene Family", *Cell* 48:681–690 (Feb. 1987).

Kohl, S. et al., "The genetic deficiency of leukocyte surface glycoprotein Mac–1, LFA–1, p150,95 in humans is associated with defective antibody–dependent cellular cytotoxicity in vitro and defective protection against herpes simplex virus infection in vivo", *J. Immunol.* 137:1688–1694 (Sep. 1986).

Krensky, A. M. et al., "Human cytolytic T–lymphocyte clones and their function–associated cell surface molecules", in: *Hybridoma Technology in the Biosciences and Medicine*, Chapter 35, pp. 559–573 (1985).

Krensky, A. M. et al., "LFA–1, LFA–2, and LFA–3 antigens are involved in CTL–target conjugation", *J. Immunol.* 132:2180–2182 (1983).

Krensky, A. M. et al., "The functional significance, distribution, and structure of LFA–1, LFA–2, and LFA–3: cell surface antigens associated with CTL–target interactions", *J. Immunol.* 131:611–614 (1983).

Kurzinger, K. et al., "Structural homology of a macrophage differentiation antigen and an antigen involved in T–cell–mediated killing", *Nature* 296:668–671 (1982).

Lasky, L. A. et al., "Cloning of a Lymphocyte Homing Receptor Reveals a Lectin Domain", *Cell* 56:1045–1055 (1989).

Livingston, D. M., "Immunoaffinity Chromatography of Proteins", *Meth. Enzymol.* 34:723–731 (1974).

Martin, P. J. et al., "Identification and functional characterization of two distinct epitopes on the human T–cell surface protein Tp50", *J. Immunol.* 131:180–185 (1983).

Miller, L. J. et al., "Regulated expression of the Mac–1, LFA–1, p150,95 glycoprotein family during leukocyte differentiation", *J. Immunol.* 137:2891–2900 (Nov. 1986).

Plunkett, M. L. et al., "Purification and characterization of the lymphocyte function–associated–2 (LFA–2) molecule", *J. Immunol.* 136:4181–4187 (Jun. 1986).

St. John, T. et al., "Expression cloning of a lymphocyte homing receptor cDNA: ubiquitin is the reactive species", *Science* 231:845–850 (Feb. 1986).

Sanchez–Madrid, F. et al., "A human leukocyte differentiation antigen family with distinct α–subunits and a common β–subunit: The lymphocyte function–associated antigen (LFA–1), the C3bi complement receptor (OKM1/Mac–1) and the p195,95 molecule", *J. Exp. Med.* 158:1785–1803 (1983).

(List continued on next page.)

*Primary Examiner*—Elizabeth Kemmerer
*Assistant Examiner*—David S. Romeo
*Attorney, Agent, or Firm*—Sterne, Kessler, Goldstein & Fox P.L.L.C.

[57] ABSTRACT

The invention relates to therapeutic methods of using a substantially pure protein comprising the β-subunit of a human glycoprotein involved in cellular adhesion, or a biologically active fragment thereof, or analog thereof. These therapeutic methods are useful for treating auto immune diseases and allograft rejection.

9 Claims, 7 Drawing Sheets

OTHER PUBLICATIONS

Sanchez–Madrid, F. et al., "Mapping of antigenic and functional epitopes on the α–and β–subunits of two related mouse glycoprotein involved in cell interactions, LFA–1 and Mac–1", *J. Exp. Med.* 158:586–602 (1983).

Sanchez–Madrid, F., "Three distinct antigens associated with human T–lymphocyte–mediated cytolysis: LFA–1, LFA–2, and LFA–3", Proc. Natl. Acad. Sci. U.S.A. 79:7489–7493 (1982).

Shaw, S. et al., "Two antigen–independent adhesion pathways used by human cytotoxic T–cell clones", *Nature* 323:262–264 (Sep. 1986).

Shuster, D. E. et al., "Identification and prevalence of a genetic defect that causes leukocyte adhesion definciency in Holstein cattle", *Proc. Natl. Acad. Sci. U.S.A.* 89:9225–9229 (1992).

Springer, T. A. et al., "The lymphocyte function–associated LFA–1, CD2, and LFA–3 molecules: cell adhesion receptors of the immune system", *Ann. Rev. Immunol.* 5:223–252 (1987).

Springer, T. A. et al., "Sequence homology of the LFA–1 and Mac–1 leukocyte adhesion glycoproteins and unexpected relation to leukocyte interferon", *Nature* 314:540–542 (1985).

Springer, T. A. et al., "Inherited LFA–1, Mac–1 definciency and its molecular biology", in: *Mononuclear Phagocytes and Inflammation*, Van Furth, R. et al., eds., Nijhoff, Dordrecht: Neth., pp. 115–123 (1985).

Springer, T. A. et al., "Inherited deficiency of the Mac–1, LFA–1, p150,95 glycoprotein family and its molecular basis", *J. Exp. Med.* 160:1901–1918 (1984).

Suggs, S. V. et al., "Use of synthetic oligonucleotides as hybridization probes: Isolation of cloned cDNA sequences for human $β_2$ microglobulin", *Proc. Natl. Acad. Sci. U.S.A.* 78:6613–6617 (1981).

Wolf, M. et al., "Monoclonal antibodies to T11, LFA–2, and LFA–3 antigens inhibit binding of human thymocytes to autologous thymic epithelial cells", *Clin. Research* 34:674A (Apr. 1986).

Young, R. A. et al., "Yeast RNA polymerase II genes: Isolation with antibody probes", *Science* 222:778–782 (1983).

Anderson, D.C. et al., "Leukocyte LFA–1, OKM1, p150,95 deficiency syndrome: functional and biosynthetic studies of three kindreds," *Fed. Proc., FASEB* 44(10):2671–2677 (Jul. 1985).

Fischer, A. et al., "Prevention of Graft Failure by an Anti–HLFA–1 Monoclonal Antibody in HLA–Mismatched Bone–Marrow Transplantation," *Lancet*:1058–1061 (Nov. 1986).

Sastre, L. et al., "A partial genomic DNA clone for the α subunit of the mouse complement receptor type 3 and cellular adhesion molecue Mac–1," *Proc. Natl. Acad. Sci. U.S.A.* 83:5644–5648 (Aug. 1986).

Hynes et al. Cell 48, 549–554, 1987.

Alberts et al. Molecular Biology of the Cell. Garland Publishing, Inc., pp. 264–266, 1983.

CAGGGCAGACTGTAGCAAA GCCCCCACGGCCCAGCCAGGA GCACCGCCGCCGGACTCCAGC ACACCGAGGGAC      17

ATG CTG GGC CTG CGC CCC CCA CTG CTC GCC CTG GTG GGG CTG CTC TCC CTC
Met Leu Gly Leu Arg Pro Pro Leu Leu Ala Leu Val Gly Leu Leu Ser Leu

GGG TGC GTC CTC TCT CAG GAG TGC Cys ACG AAG TTC AAG GTC AGC AGC TGC Cys CGG GAA      53
Gly Cys Val Leu Ser Gln Glu Cys     Thr Lys Phe Lys Val Ser Ser Cys     Arg Glu

TGC ATC GAG TCG GGG CCC GGC TGC Cys ACC TGG TCC CAG AAG CTG AAC TTC ACA GGG
Cys Ile Glu Ser Gly Pro Gly Cys     Thr Trp Cys     Gln Lys Leu Asn Phe Thr Gly

CCG GAT CCT GAC TCC ATT CGC AGG Cys TGC GAC ACC CGG CCA CAG CTG CTC ATG AGG      89
Pro Asp Pro Asp Ser Ile Arg Arg Cys Cys Asp Thr Arg Pro Gln Leu Leu Met Arg

GGC TGT GCG GCT GAC GAC ATC ATG GAC CAG CCC ACA AGC CTC GCT GAA ACC CAG GAA
Gly Cys Cys Ala Ala Asp Asp Ile Met Asp Gln Pro Thr Ser Leu Ala Glu Thr Gln Glu

GAC CAC AAT GGG GGC CAG AAG GGC CAG AAG CTG TCC CCA CAA AAA GTG ACG CTT TAC CTG      125
Asp His Asn Gly Gly Gln Lys Gly Gln Lys Leu Ser Pro Gln Lys Val Thr Leu Tyr Leu

CGA CCA GGC CAG GCA GCA GCG TTC AAC GTG ACC TTC CGG CGG GCC AAG GGC TAC
Arg Pro Gly Gln Ala Ala Ala Phe Asn Val Thr Phe Arg Arg Ala Lys Gly Tyr

CCC ATC GAC CTG TAC TAT CTG ATG GAC CTC TCC TAC TCC ATG CTT GAT GAC CTC
Pro Ile Asp Leu Tyr Tyr Leu Met Asp Leu Ser Tyr Ser Met Leu Asp Asp Leu

FIG.1A

```
AGG AAT GTC AAG AAG CTA GGT GGC GAC CTG CTC CGG GCC CTC AAC GAG ATC ACC      161
Arg Asn Val Lys Lys Leu Gly Gly Asp Leu Leu Arg Ala Leu Asn Glu Ile Thr

GAG TCC GGC CGC ATT GGC TTC GGG TCC TTC GTG GAC AAG ACC GTG CTG CCG TTC      197
Glu Ser Gly Arg Ile Gly Phe Gly Ser Phe Val Asp Lys Thr Val Leu Pro Phe

GTG AAC ACG CAC CCT GAT AAG CTG CGA AAC CCA TGC Cys CCC AAC AAG GAG AAA GAG  233
Val Asn Thr His Pro Asp Lys Leu Arg Asn Pro Cys Pro Asn Lys Glu Lys Glu
                                        L-56a

TGC CAG CCC CCG TTT GCC TTC AGG CAC GTG CTG AAG CAG CTG ATT TCC GGA AAC TCC AAC  269
Cys Gln Pro Pro Phe Ala Phe Arg His Val Leu Lys Gln Leu Ile Ser Gly Asn Ser Asn

CAG TTT CAG ACC GAG GTC GGG AAG ATG ATG CAG GTC GCC GCC TGC Cys CCC GAG GAA ATC GGC   556
Gln Phe Gln Thr Glu Val Gly Lys Met Met Gln Val Ala Ala Cys Pro Glu Glu Ile Gly

GAG GGT GGG CTG GAC GCC ATG ATG CAG GTC GCC GCC TGC Cys CCC GAG GAA ATC GGC   664
Glu Gly Gly Leu Asp Ala Met Met Gln Val Ala Ala Cys Pro Glu Glu Ile Gly

TGG CGC AAC GTC ACG ACG CGG CTG CTG GTG TTT GCC ACT GAT GAC GGC TTC CAT TTC   772
Trp Arg Asn Val Thr Thr Arg Leu Leu Val Phe Ala Thr Asp Asp Gly Phe His Phe
                                                            M-58

GCC GGC GAC GGA AAC CTG GCC ATC CTG ACC CCC AAC GAC CTC ACC CCC AAC GAC GGC CGC TGT Cys CAC   880
Ala Gly Asp Gly Lys Leu Gly Ala Ile Leu Thr Pro Asn Asp Gly Arg Cys His
```

FIG.1B

```
 988  CTG GAG GAC AAC TTG TAC AAG AGG AGC AAC GAA TTC GAC TAC CCA TCG GTG GGC                                    305
      Leu Glu Asp Asn Leu Tyr Lys Arg Ser Asn Glu Phe Asp Tyr Pro Ser Val Gly

CAG CTG GCG CAC AAG CTG GCT GAA AAC ATC CAG CCC ATC TTC GCG GTG ACC
      Gln Leu Ala His Lys Leu Ala Glu Asn Ile Gln Pro Ile Phe Ala Val Thr
                                                              P-61
      AGT AGG ATG GTG AAG ACC TAC TAT GAG AAA CTC ACC GAG ATC ATC CCC AAG TCA GCC                                341
      Ser Arg Met Val Lys Thr Tyr Tyr Glu Lys Leu Thr Glu Ile Ile Pro Lys Ser Ala
              M-52

1096  GTG GGG GAG CTG TCT GAG GAC TCC AGC AAT GTG GTC CAT CTC ATT AAG AAT GCT
      Val Gly Glu Leu Ser Glu Asp Ser Ser Asn Val Val His Leu Ile Lys Asn Ala

TAC AAT AAA CTC TCC TCC AGG GTC TTC CTG GAT CAC AAC GCC CTC CCC GAC ACC                                    377
      Tyr Asn Lys Leu Ser Ser Arg Val Phe Leu Asp His Asn Ala Leu Pro Asp Thr
                                                   L-65
1204  CTG AAA GTC ACC TAC GAC TCC TTC TGC AGC AAT GGA GTG ACG CAC AGG AAC CAG
      Leu Lys Val Thr Tyr Asp Ser Phe Cys Ser Asn Gly Val Thr His Arg Asn Gln

CCC AGA GGT GAC TGT GAT GGC GTG CAG ATC AAT GTC CCG ATC ACC TTC CAG GTG                                    413
      Pro Arg Gly Asp Cys Asp Gly Val Gln Ile Asn Val Pro Ile Thr Phe Gln Val

1312  AAG GTC ACG GCC ACA GAG TGC ATC CAG GAG CAG TCG TTT GTC ATC CGG GCG CTG
      Lys Val Thr Ala Thr Glu Cys Ile Gln Glu Gln Ser Phe Val Ile Arg Ala Leu
```

FIG.1C

```
                                                                                          449
      GGC TTC ACG GAC ATA GTG ACC GTG CAG GTT CTT CCC CAG TGT GAG TGC CGG TGC
      Gly Phe Thr Asp Ile Val Thr Val Gln Val Leu Pro Gln Cys Glu Cys Arg Cys
1420  CGG GAC CAG AGC AGA GAC CGC AGC CTC TGC CAT GGC AAG GGC TTC TTG GAG TGC
      Arg Asp Gln Ser Arg Asp Arg Ser Leu Cys His Gly Lys Gly Phe Leu Glu Cys
                                                                                          485
      GGC ATC TGC AGG TGT GAC ACT GGC TAC ATT GGG AAA AAC TGT GAG TGC CAG ACA
      Gly Ile Cys Arg Cys Asp Thr Gly Tyr Ile Gly Lys Asn Cys Glu Cys Gln Thr
                     ────P-20────
1528  CAG GGC CGG AGC CAG AGC CTG GAA GGA CTG GAG CTG TGC CGG AAC GAC AAC TCC
      Gln Gly Arg Ser Gln Ser Leu Glu Gly Leu Glu Leu Cys Arg Asn Asp Asn Ser
                                        ────P-18────
                                                                                          521
      ATC ATC TGC TCA GGG CTG GGG GAC TGT GTC TGC GGG CAG TAC TGC CTG CAC ACC
      Ile Ile Cys Ser Gly Leu Gly Asp Cys Val Cys Gly Gln Tyr Cys Leu His Thr
1636  AGC GAC GTC CCC GGC AAG CTG ATA TAC GGG CAG TAC TGC GAG TGT GAC ACC ATC
      Ser Asp Val Pro Gly Lys Leu Ile Tyr Gly Gln Tyr Cys Glu Cys Asp Thr Ile
                                                              ──L-56b──
                                                                                          557
      AAC TGT GAG CGC TAC AAC GGC CAG GTC TGC GGC GGC CCG GGC AGG GGC CTC TGC
      Asn Cys Glu Arg Tyr Asn Gly Gln Val Cys Gly Gly Pro Gly Arg Gly Leu Cys
1744  TTC TGC AAG TGC CCC TGC CAC CCG GGC TTT GAG GGC TCA GCG TGC CAG TGC
      Phe Cys Lys Cys Pro Cys His Pro Gly Phe Glu Gly Ser Ala Cys Gln Cys
```

FIG.1D

```
        GAG AGG ACC ACT GAG GGC TGC CTG AAC CCG CGT GTT GAG TGT ACT GGT CGT
        Glu Arg Thr Thr Glu Gly Cys Leu Asn Pro Arg Val Glu Cys Ser Gly Arg    593

1852    GGC CGG TGC CGC TGC AAC GTA TGC GAG TGC CAT TCA GGC TAC CAG CTG CCT CTG
        Gly Arg Arg Cys Asn Val Cys Glu Cys His Ser Gly Tyr Gln Leu Pro Leu

TGC CAG GAG TGC CCC GGC TCA CCC TGT GGC AAG TAC TAT ATC TCC TGC GCC
        Cys Gln Glu Cys Pro Gly Pro Ser Pro Cys Gly Lys Tyr Tyr Ile Ser Cys Ala    629

1960    GAG TGC CTG AAG TTC GAA AAG GGC CCC TTT GGG AAG AAC TGC AGC GCG GGG TGT
        Glu Cys Leu Lys Phe Glu Lys Gly Pro Phe Gly Lys Asn Cys Ser Ala Ala Cys

CCG GGC CTG CAG CTG TCG AAC AAC CCC GTG AAG GGC AGG ACC TGC AAG GAG AGG
        Pro Gly Leu Gln Leu Ser Asn Asn Pro Val Lys Gly Arg Thr Cys Lys Glu Arg    665

2068    GAC TCA GAG GGC TGC TGG GTG GCC TAC ACG CTG GAG CAG CAG GAC GGG ATG GAC
        Asp Ser Glu Gly Cys Trp Val Ala Tyr Thr Leu Glu Gln Gln Asp Gly Met Asp

CGC TAC CTC ATC TAT GTG GAT GAG AGC CGA GAG TGT GTG CCA GGC CCC AAC ATC
        Arg Tyr Leu Ile Tyr Val Asp Glu Ser Arg Glu Cys Val Ala Gly Pro Asn Ile    701

2176    GCC GCC ATC GTC GGG GGC ACC GTG GCA GGC ATC GTG CTG ATC GGC ATT CTC CTG
        Ala Ala Ile Val Gly Gly Thr Val Ala Gly Ile Val Leu Ile Gly Ile Leu Leu
```

FIG.1E

```
        CTG GTC ATC TGG AAG GCT CTG ATC CAC CTG AGC GAC CTC CGG GAG TAC AGG CGC        737
        Leu Val Ile Trp Lys Ala Leu Ile His Leu Ser Asp Leu Arg Glu Tyr Arg Arg

2284    TTT GAG GAG AAG CTC AAG TCC CAG TGG AAC AAT GAT AAT CCC CTT TTC AAG
        Phe Glu Glu Lys Leu Lys Ser Gln Trp Asn Asn Asp Asn Pro Leu Phe Lys

AGC GCC ACC ACG ACG GTC ATG AAC CCC AAG TTT GCT GAG AGT TAG GAGCACTTGGT          769
        Ser Ala Thr Thr Thr Val Met Asn Pro Lys Phe Ala Glu Ser  *

2403    GAAGACAAGGCCGTCAGGACCCACCATGTCTGCCCCATCACGGGGCCGAGACATGGCTTGGCCACAGCTCT

TCAGGATGTCACCAATTAACCAGAAATCCAGTTATTTCCGCCCTCAAATGACAGCCATGGCCGGCCCGGTG

2546    CTTCTCGGGCTCGTCGGGGACAGCTCCACTCTGACTCTTGCATGGAGACTTGAGGAGG

CTTGAGGTTGGTGAGGTTAGGTGCGTGTTTCCTGTGCAAGTCAGGACATCAGTCTGATTAAAGGTGTGCCA

2689    ATTTATTTACATTTAAACTTGCTCAGGGTATAAAATGACATCCATTAATTATATTGTTAATCAATCACGTGT

ATAGAAAAAAAAATAAAACTTCAAT    2776
```

FIG.1F p150,95 β Subunit

P-61 sequence            L Y E N N I Q P I F A V T S
    Deduced sequence     K L A E N N I Q P I F A V T S P-20 sequence            (T/C) D T G Y I G K
    Deduced sequence     R  C  D T G Y I G K P-18 sequence            S S Q E L E G S(T/C) (R)
    Deduced sequence     R S S Q E L E G S  C    R Mac-1 β Subunit M-58 sequence            L L V F A T D D G F H F
    Deduced sequence     R L L V F A T D D G F H F M-52 sequence            X A V G E L S E X(S) X N
    Deduced sequence     K S A V G E L S E D S S N LFA-1 β Subunit L56a sequence            E C Q P P F A F R
    Deduced sequence     K E C Q P P F A F R L56b sequence            L I Y G Q Y C E(C) D T I
    Deduced sequence     K L I Y G Q Y C E C D T I L-65 sequence            V F L D H N A L P
    Deduced sequence     R V F L D H N A L P

FIG. 2

METHODS FOR TREATING VARIOUS DISEASE STATES BY REDUCING ADHESION OF LEUKOCYTES OF TARGET CELLS

This application is a division of application Ser. No. 08/223,820, filed Apr. 6, 1994, U.S. Pat. No. 5,739,032; which is a continuation of application Ser. No. 07/771,849, filed Oct. 7, 1991 now abandoned; which is a continuation of application Ser. No. 07/019,440, filed Feb. 26, 1987, now abandoned.

The work described herein was performed with the aid of government funding, and the government therefore has certain rights in the invention. Specifically, the work was supported by N.I.H. grants CA 31798 and AI 05877.

BACKGROUND OF THE INVENTION

This invention relates to cellular adhesion.

Cellular adhesion is a critical function for guiding migration and localization of cells, and for maintaining the integrity of the body. Receptors for extracellular matrix components such as fibronectin, laminin, and vitronectin mediate cellular adhesion during morphogenesis and wound healing. In the immune system, regulatory networks require intimate cell—cell interaction among lymphocytes and antigen-presenting accessory cells, and cell-mediated cytolysis involves direct contact between the effector cell and virally-infected or transformed target cells. Leukocyte-endothelial interactions are important in leukocyte mobilization into inflammatory sites and in lymphocyte recirculation. These cellular adhesion reactions are mediated in part by a family of structurally related glycoproteins, LFA-1, Mac-1, and p150,95, all of which share a common β-subunit (hereinafter referred to as the β-subunit of human LFA-1). Springer et al., 314 Nature 540, 1985; Springer et al., "The lymphocyte function-associated LFA-1, CD2, and LFA-3 molecules: cell adhesion receptors of the immune system" Ann. Rev. Immunol. Vol. 5, 1987; both hereby incorporated by reference.

SUMMARY OF THE INVENTION

In general, the invention features a) substantially pure recombinant β-subunit of a human glycoprotein concerned with cellular adhesion, or b) a biologically active fraction of this β-subunit, c) an analog of the β-subunit, or c) a fragment of the β-subunit, composed of at least 10% of a contiguous sequence of the β-subunit. The invention also features a cDNA sequence encoding for the β-subunit; and a vector containing a DNA sequence encoding therefor. By recombinant subunit is meant the polypeptide product of recombinant DNA encoding the β-subunit, i.e., the polypeptide expressed from DNA which is not in its naturally occuring location within a chromosome. By natural subunit is meant that subunit produced naturally in vivo from naturally occuring and located DNA. By analog is meant a polypeptide differing from the normal polypeptide by one or more amino acids, but having substantially the biological activity of the normal polypeptide. The invention also features any monoclonal antibody (MAb) raised against the recombinant β-subunit, a biologically active fraction, an analog, or a fragment thereof composed of at least 10%, preferably at least 80%, of a contiguous sequence of the β-subunit of a human glycoprotein.

The CDNA sequence encoding the LFA-1 β-subunit or a fragment thereof may be derived from any of the naturally occuring genes encoding it, or synthesized chemically. Variations in this sequence which do not alter the amino acid sequence of the resulting protein, or which do not significantly alter the biological activity of the protein, are also acceptable, and are within this invention.

Preferably the human glycoprotein is LFA-1, Mac-1 or p150,95.

As will be described in more detail below, the invention permits the diagnosis and treatment of a variety of human disease states.

Other features and advantages of the invention will be apparent from the following description of the preferred embodiments thereof and from the claims.

DESCRIPTION OF THE PREFERRED EMBODIMENTS

The drawings are first briefly described.

DRAWINGS

FIG. 1 is the DNA coding sequence of the β-subunit of LFA-1, Mac-1 and p150,95. Potential N-glycosylation sites are marked with triangles.

FIG. 2 is a comparison of the amino acid sequence predicted from the cDNA in FIG. 1, and the amino acid sequence derived from enzyme digests of the β-subunit of LFA-1. Ambiguous determinations of amino acids are bracketed. The code for amino acids is as follows:

| Ala, | A | -alanine |
|---|---|---|
| Arg, | R | -arginine |
| Asn, | N | -asparagine |
| Asp, | D | -aspartic acid |
| Cys, | C | -cysteine |
| Gln, | Q | -glutamine |
| Glu, | E | -glutamic acid |
| Gly, | G | -glycine |
| His, | H | -histidine |
| Ile, | I | -isoleucine |
| Leu, | L | -leucine |
| Lys, | K | -lysine |
| Met, | M | -methionine (start) |
| Phe, | F | -phenylalanine |
| Pro, | P | -proline |
| Ser, | S | -serine |
| Thr, | T | -threonine |
| Trp, | W | -tryptophan |
| Tyr, | Y | -tryosine |
| Val, | V | -valine |

Methods

In general, the β-subunit of any of the above described related glycoproteins is isolated by standard procedures and the amino acid sequence of at least a part of it determined. From this analysis a synthetic oligonucleotide probe, corresponding to the amino acid sequence, is synthesized and used as a probe for a genomic or cDNA library containing a DNA sequence encoding the β-subunit. An example of this procedure is given below. One skilled in the art will realize that this represents only one of many methods which can be used to achieve cloning of the gene encoding the LFA-1 β-subunit.

Purification of the β-Subunit

MAb's directed against the alpha subunits of p150,95, Mac-1, and LFA-1, were used to affinity purify their respective proteins from three different sources. The p150,95 protein was purified from hairy cell leukemia spleens (Miller et al., 1986, 137 J. Immunol. 2891, hereby incorporated by reference); Mac-1 was purified from pooled human leukocytes (Miller et al., *supra*); and LFA-1 was purified from the SKW3 T cell line using TS1/22 monoclonal antibody (Sanchez-Madrid et al. 1983, J. Exp. Med. 158:586, hereby incorporated by reference).

Preparative SDS-PAGE gels were run using the method of Laemmli (Hunkapiller et al., 1983, Meth. Enzym. 91:227). 0.1 mM Na Thioglycolate was added to the upper chamber to reduce the level of free radicals in the gel. Bands were visualized by soaking the gel for several minutes in 1M KCl and then excised. The β-subunit was electroeluted using the apparatus and method described by Hunkapillar et al., *supra*. The purified protein was reduced with 2 mM DTT in the presence of 2% SDS and alykylated with 5 mM iodoacetic acid in the dark. (In some cases, the protein was reduced and alkylated prior to running the preparative gel.)

Amino acid sequencing

The above samples were precipitated using four volumes of ethanol at −20° C. for 16 hr, and the protein pellet redissolved in 30–50 μl of 0.1M $NH_4CO_3$ containing 0.1 mM $CaCl_2$ and 0.1% zwitterent 3–14 (Calbiochem, San Diego, Calif.). The sample was then digested with 1% w/w trypsin for 6 hr at 37° C. At 2 and 4 hr during the incubation, additional trypsin (1% w/w) was added.

The tryptic peptides were resolved by reverse phase HPLC (Beckman Instruments) with a 0.4×15 cm C4 column (Vydac, Hesperig, Calif.), and eluted from a 2 hr linear gradient from 0 to 60% acetonitrile. 0.1% TFA was included in both the aqueous and organic solvents. The peaks were monitored at 214 and 280 nm and collected into 1.5 ml polypropylene tubes. The fractions were concentrated to 30 μl or less on a speed-vac apparatus, and selected peptides subjected to sequence analysis using a gas phase microsequenator (Applied Biosystems, Foster City, Calif.).

EXAMPLE

β-subunit of p150,95 p150,95 was affinity purified from the spleens of human patients with hairy cell leukemia using a monoclonal antibody specific for the alpha subunit (MW approx. 150,000, Miller et al., *supra*). Analysis of the purified protein by SDS-PAGE and silver staining revealed the characteristic alpha and beta subunit, with no significant amounts of contaminating proteins. The β-subunit band was excised from a preparative SDS-PAGE gel and electroeluted, as described above.

The N-terminus of the beta subunit was blocked and therefore could not be sequenced. Internal amino acid sequence information was obtained by digesting the β-subunit with trypsin. The tryptic peptides were resolved by reverse phase HPLC and eluted on a 60% acetonitrile gradient. Peaks analyzed by absorbance at 214 and 280 nm were collected and applied to a gas phase microsequenator.

The peptide sequences of two of these fragments is:

P-61 Peptide Sequence: LeuTyrGluAsnAsnIleGlnProIlePheAlaValThrSer

P-20 Peptide Sequence: ThrAspThrGlyTyrIleGlyLys.

Two strategies were adopted for constructing oligonucleotide probes. A unique sequence 39mer was designed from peptide P-61 based on human codon usage frequency (Lathe, 1985, J. Mol. Biol. 183:1). Its sequence is:

3'-GACATACTCTTGTTGTAGGTCGGGTAGAAACGACACTGG-5'.

In addition, two sets of mixed sequence probes were constructed such that every possible sequence was represented. A 20mer of 96-fold redundancy was derived from peptide P-61, and a 17mer of 192-fold redundancy was constructed based on the sequence from a different peptide fragment of the β-subunit, P-20. These sequences are given below.

```
20mer, Mixed Sequence 3'- ATACTATTATTATAAGTCCC -5'
                           G  C  G  G   C  T
                                         G 17mer, Mixed Sequence 3'- CTATGACCAATATAACC    -5'
                          G  C  C  G  G
                          G  G        T
                          T  T
```

The 39mer and the mixed sequence 20mer were used to probe a Northern blot of poly A+selected RNA from PMA-activated U937 cells. The U937 cells, JY lymphoblastoid cells, HeLa cells, and CO3 cells (Springer et al., 1984, J. Exp. Med. 160:1901, an EBV-transformed cell line from a healthy donor) were grown in RPMI 1640 containing 10–15% fetal calf serum in a humidified atmosphere of 5% $CO_2$ and 37° C. The U937 cells were activated with 2 ng/ml PMA for three days prior to harvesting. The cells were lysed in a 4M guanidinium isothiocyanate solution, and RNA isolated in a 5.7M CsCl gradient. Poly A+ mRNA was selected with oligo (dT)-cellulose columns (Maniatis et al., Molecular Cloning: A laboratory manual, Cold Spring Harbor Laboratory, N.Y., 1982) or oligo (dT)-affinity paper (Amersham). This RNA was denatured and sized on a 1% agarose gel containing formaldehyde (Maniatis et al., *supra*) and transferred to nylon membranes (BioRad) in 20X SSC. A lane containing 28S and 18S ribosomal RNA from human cells or 23S and 16S rDNA from *Escherichia coli* was run to provide molecular weight standards.

The filters were hybridized with nick-translated probe DNA at 42° C. for 18 hr in 5×SSPE, 50% formamide, 10% dextran sulfate, 1×Denhardts, 0.5% SDS and 100 ug/ml denatured salmon sperm DNA, and washed at high stringency (65° C.) in 0.2×SSC and 0.1% SDS. Both probes identified a band of approximately 3 kb. The 39mer gave a much stronger signal and was chosen for the primary screening of a cDNA library.

A human tonsil cDNA library (gift of L. Klickstein) was size-selected for inserts of 2 kb or greater and constructed in λgt11 (Wong et al., 1985, Proc. Nat. Acad. Sci. U.S.A. 82:7711). The original library of 4×10⁶ recombinants was amplified once, and 200,000 recombinants plated at a density of 7500 plaques/100 mm plate. The plaques were amplified in situ on duplicate nitrocellulose filters, as described by Woo (1979, Meth. Enzym. 68:389).

The oligonucleotide probes were labeled with $^{32}$P-ATP using polynucleotide kinase. The filters were prehybridized for at least 2 hr at 42° C. in 6×SCC, 1×Denhardts, 0.5% SDS, 0.05% phosphate buffer, and 100 μg/ml of salmon sperm DNA. Hybridization with the 39mer was overnight at 42° C. in prehybridization solution containing 20 μg/ml tRNA. The filters were washed at 53° C. to 55° C. with 6 X SSC, 0.1% SDS, and 0.05% phosphate buffer. The damp filters were covered with plastic wrap and exposed to film with an intensifying screen. Phage that gave positive signals on duplicate filters were plaque purified and rescreened with the 39mer at a higher wash temperature (60° C.) and with 20mer and 17mer mixed sequence probes. 15 positive clones were picked. Eight of the clones crossreacted with each other and gave positive signals with the 20mer mixed sequence probe and the independent 17mer mixed sequence probe. These clones were chosen for further analysis.

To confirm the identity of the cDNA clones, a 263 bp PstI/EcoRI restriction fragment which hybridized to the 39mer was subcloned into M13 vector and sequenced by the Sanger dideoxy chain termination method as follows. The amino acid sequence deduced from the DNA sequence is identical in 13 of 14 positions to the peptide sequence from which the 39mer probe was derived, including one amino acid which was not included in the design of the oligonucleotide. Furthermore, the predicted amino acid sequence shows that this peptide is preceded by a lysine and followed by an arginine, as expected for a tryptic fragment. The one mismatch may be due to normal polymorphism. The unique sequence oligonucleotide was 87% homologous to the cDNA sequence, despite the one amino acid mismatch.

The cDNA clones were restriction mapped by single and double restriction digests and, after end-labeling, by partial restriction digests (Maniatis et al., *supra*). Compatible restriction fragments were subcloned directly into M13 cloning vectors. Other fragments were first blunt ended with Klenow, T4 polymerase, or Mung Bean nuclease (Maniatis et al., *supra*) and ligated into the HincII or SmaI site of the M13 polylinker. The nucleotide sequence of both strands was determined by the dideoxy chain termination method of Sanger et al. (1977, Proc. Nat. Acad. Sci. U.S.A. 74:5463) using $^{35}$S-dATP.

The complete nucleotide sequence and deduced amino acid sequence of the β-subunit gene in the longest clone, 18.1.1 (2.8 kb is length), is shown in FIG. 1. The first ATG is at position 73, and the sequence surrounding the ATG is consistent with the consensus rules for an initiation codon (Kozak 1984, Nucl. Acid. Res. 12:857). This putative initiation codon is followed by an open reading frame of 2304 bp, which could encode a polypeptide of 769 amino acids (aa). The stop codon ATC is followed by a 3' untranslated region of 394 bp. The poly A tail was not found, although a consensus polyadenylation signal (AATAAA) is located 9 bp from the 3' end.

The deduced amino acid sequence of the cDNA clones was compared to peptide sequence data from the beta subunit of Mac-1, LFA-1, and p150,95 (FIG. 2). In addition to the P61 and P-20 peptide sequences given above, one other peptide was sequenced from the beta subunit of p150,95. Tryptic peptides were also prepared and analyzed from the beta subunit of purified Mac-1 and LFA-1. Each peptide sequence is found within the deduced amino acid sequence (FIGS. 1 and 2). Thus, it can be concluded that the cDNA encodes the β-subunit of human LFA-1.

The cDNA clones hybridize to a single mRNA species of approximately 3.0 kb, which is the same message identified by the 39mer oligonucleotide. This message is present in PMA-activated U937 cells (LFA-1$^+$, Mac-1$^+$, p150,95$^+$), JY lymphoblastoid cells (LFA-1$^+$, Mac-1$^-$, p150,95$^-$), and EBV-transformed cells from a normal donor (LFA-1$^+$, Mac-1$^-$, p150,95$^-$), but is absent in HeLa cells (LFA-1$^-$, Mac-1$^-$, $_p$150, 95$^-$). Although clone 18.1.1 lacks the poly A tail, it is close to the estimated size of the RNA message.

Within the deduced polypeptide are two regions of sufficient length and hydrophobicity that could span the membrane bilayer. The first domain, which begins with the putative initiation methionine and extends 22 amino acids, has the characteristics of a signal sequence. This putative signal sequence is followed by a charged glutamine, a residue which is often cyclized at the N-terminal position. This would be consistent with the N-terminal blockage of the β-subunit, if the signal sequence is cleaved during processing.

Use

The cDNA encoding the β-subunit of human LFA-1 can be used to produce recombinant β-subunit in large amounts. For example, the beta-subunit-encoding cDNA can be excised from the λgt11 clones and introduced into an expression vector (plasmid, cosmid, phage or other type) to express the β-subunit in *E. coli*, using standard techniques. Alternatively the clones may be inserted into other vectors, such as mammalian, insect, or yeast expression vectors, and used to produce recombinant β-subunit in mammalian or yeast cells.

The subunits produced by the above methods can be readily purified and used as an immunogen to raise monoclonal antibodies to the subunits. These antibodies can be labelled and used in standard immunoassays to monitor the level of LFA-1, Mac-1, or p150,95 in white blood cells, and in the serum or other body fluids of patients having medical disorders associated with too many or too few cells having on their surfaces LFA-1 or related proteins. For example, diseases, e.g., AIDS, characterized by immunosuppression can be expected to be accompanied by abnormally low levels of such cells, which are instrumental in fighting infections, and such diseases can thus be monitored by monitoring levels of these proteins. Also, other disease states, e.g., autoimmune disease, allograft rejection, and graft-versus-host disease, can be expected to be characterized by abnormally high levels of such cells, and thus also can be monitored by monitoring levels of these proteins. They can also be used to diagnose leukocyte adhesion deficiency, an inherited deficiency in the LFA-1, Mac-1, and p150,95 glycoproteins. Antibodies to the β-subunit can also be used to purify LFA-1 or related proteins by conventional immunoaffinity purification methods.

The purified proteins, particularly LFA-1, Mac-1 and/or p150,95, whether native or recombinant, can also be used therapeutically. The proteins can be administered to patients in need of such treatment in an effective amount (e.g., from 20–500 μg per kg body weight), and mixed with a pharmaceutically acceptable carrier substance such as saline. Therapeutic utility of these proteins is based on the fact that disease states such as autoimmune diseases, allograft rejections, and graft-versus-host diseases involve abnormally high levels of cell-to-cell contact mediated by the recognition and binding of LFA-1 and related proteins to target antigen presenting cells, endothelial cells, and other types of cells. The administration of LFA-1 or a related protein, or fragments thereof, will compete for receptors for the cell-bound protein, inhibiting cell-to-cell binding and thus bringing about the desired immunosuppression. A particular disease for which these proteins will be useful is the autoimmune disease rheumatoid arthritis. Preferably administration is intravenous at about 20–500 μg per kg body weight, or directly at an inflamed joint of a patient suffering from rheumatoid arthritis. Alternatively, oral administration or local application can be used by providing tablets, capsules, or solutions, or by applying lotions as required. The amount and method of administration will vary dependent upon the age and weight of the patient, and the disease to be treated. Other automimmune diseases which can be treated include systemic lupus erythematosis, juvenile onset diabetes, multiple sclerosis, allergic conditions, eczema, ulcerative colitis, inflammatory bowel disease, Crohn's disease, as well as allograft rejections (e.g., rejection of a transplanted kidney or heart). LFA-1, Mac-1, and p150,95 noramlly act in situ by binding to endothelial and other cells. Thus, the free proteins or peptides, which are administered, will be able to inhibit leukocyte immune responses and migration to inflammatory sites.

The β subunit CDNA clone can be used in prenatal diagnosis of leukocyte adhesion deficiency (LAD). LAD disease is a deficiency in cell surface expression of LFA-1, Mac-1, and p150,95 and is due at least in part to a primary genetic lesion in the β subunit. Patients with the severe form of LAD disease suffer from recurrent bacterial infections and rarely survive beyond childhood. The defect can be detected early in pregnancy since it is associated with a unique restriction fragment length polymorphism. PstI digestion of human DNA and hybridization with the 1.8 kb EcoRI fragment (shown in FIG. 2) of the β subunit cDNA defines a restriction fragment length polymorphism (RFLP). Diagnosis of this disease is therefore performed by standard procedure using the whole or a part of this EcoRI fragment. The genomic DNAs of the parents of the fetus, and the fetus are screened with this probe and an analysis of their RFLPs made. In this way the probability that the fetus has the disease can be estimated.

Other embodiments are within the following claims.

We claim:

1. A method for inhibiting a LFA-1, MacI, or p150,90 mediated leukocyte immune response in an animal comprising administering to said animal a pharmaceutical composition comprising a fragment of the extracellular domain of the β subunit of LFA-1 in admixture with a pharmaceutically acceptable carrier, wherein said fragment inhibits said leukocyte immune response and said pharmaceutical composition comprises an amount of said fragment effective for inhibiting said leukocyte immune response.

2. The method of claim 1, wherein said animal is suffering from a disease selected from the group consisting of an autoimmune disease, allograft rejection, and graft-versus-host disease.

3. The method of claim 2, wherein said disease is selected from the group consisting of: systemic lupus erythematosis, juvenile onset diabetes, multiple sclerosis, allergic conditions, eczema, ulcerated colitis, inflammatory bowel disease, and Crohn's disease.

4. The method of claim 2, wherein said disease is rheumatoid arthritis.

5. A method for inhibiting a LFA-1, Mac1, or p150,90 mediated leukocyte immune response in an animal comprising administering to said animal a pharmaceutical composition comprising the extracellular domain of the β subunit of LFA-1 in admixture with a pharmaceutically acceptable carrier, wherein said pharmaceutical composition comprises an amount of said extracellular domain effective for inhibiting said leukocyte immune response.

6. The method of claimed in claim 5, wherein said extracellular domain comprises amino acids 23–700 of FIG. 1.

7. The method of claim 5, wherein said animal is suffering from a disease selected from the group consisting of an autoimmune disease, allograft rejection, and graft-versus-host disease.

8. The method of claim 7, wherein said disease is selected from the group consisting of: systemic lupus erythematosis, juvenile onset diabetes, multiple sclerosis, allergic conditions, eczema, ulcerated colitis, inflammatory bowel disease, and Crohn's disease.

9. The method of claim 7, wherein said disease in rheumatoid arthritis.

* * * * *

UNITED STATES PATENT AND TRADEMARK OFFICE
CERTIFICATE OF CORRECTION

Page 1 of 2

PATENT NO. : 5,948,758

DATED : September 7, 1999

INVENTORS : Springer et al.

It is certified that an error appears in the above-identified patent and that said Letters Patent is hereby corrected as shown below.

On page 1, left column, in the Title, please delete "LEUKOCYTES OF TARGET CELLS" and insert therein --LEUKOCYTES TO TARGET CELLS--.

On page 1, left column, after the Assignee heading, please delete "Dana Faber" and insert therein --Dana Farber--.

In column 1, in the Title, please delete "LEUKOCYTES OF TARGET CELLS" and insert therein --LEUKOCYTES TO TARGET CELLS--.

In column 2, line 19, please delete "FIG. 1" and insert therein --Figures 1A to 1F--.

In column 2, line 23, please delete "FIG. 1" and insert therein --Figures 1A to 1F--.

In column 5, line 23, please delete "FIG. 1" and insert therein --Figures 1A to 1F--.

In column 7, line 15, please delete "MacI" and insert therein --Mac-1--.

In column 7, line 15, please delete "p150,90" and insert therein --p150,95--.

In column 8, line 6, please delete "Mac1" and insert therein --Mac-1--.

In column 8, line 6, please delete "p150,90" and insert therein --p150,95--.

In column 8, line 14, please delete "claimed in".

UNITED STATES PATENT AND TRADEMARK OFFICE
CERTIFICATE OF CORRECTION

Page 2 of 2

PATENT NO. : 5,948,758
DATED : September 7, 1999
INVENTOR(S) : Springer, et al.

It is certified that error appears in the above-identified patent and that said Letters Patent is hereby corrected as shown below:

In column 8, 15-16, please delete "FIG.1" and insert therein --Figures 1A to 1F--.

Signed and Sealed this

Seventeenth Day of April, 2001

Attest:

NICHOLAS P. GODICI

Attesting Officer

Acting Director of the United States Patent and Trademark Office